(12) United States Patent
Alnabari et al.

(10) Patent No.: US 7,544,805 B2
(45) Date of Patent: Jun. 9, 2009

(54) STABLE AMORPHOUS FORMS OF MONTELUKAST SODIUM

(75) Inventors: Mohammed Alnabari, Hura (IL); Yana Sery, Beer Sheva (IL); Itai Adin, Beer Sheva (IL); Oded Arad, Rehovot (IL); Joseph Kaspi, Givatayim (IL)

(73) Assignee: Chemagis Ltd., Bnei-Brak (IL)

( * ) Notice: Subject to any disclaimer, the term of this patent is extended or adjusted under 35 U.S.C. 154(b) by 456 days.

(21) Appl. No.: 11/048,746

(22) Filed: Feb. 3, 2005

(65) Prior Publication Data

US 2005/0187245 A1 Aug. 25, 2005

Related U.S. Application Data

(60) Provisional application No. 60/541,052, filed on Feb. 3, 2004.

(51) Int. Cl.
C07D 215/12 (2006.01)
A61K 31/47 (2006.01)

(52) U.S. Cl. .................................. 546/174; 514/311

(58) Field of Classification Search ................ 546/174; 514/311
See application file for complete search history.

(56) References Cited

U.S. PATENT DOCUMENTS

| | | | |
|---|---|---|---|
| 655,365 A | 8/1900 | Johnson | |
| 4,308,351 A | 12/1981 | Leighton et al. | |
| 4,729,949 A | 3/1988 | Weinreb et al. | |
| 4,894,343 A | 1/1990 | Tanaka et al. | |
| 5,059,266 A | 10/1991 | Yamane et al. | |
| 5,204,055 A | 4/1993 | Sachs et al. | |
| 5,272,081 A | 12/1993 | Weinreb | |
| 5,395,588 A | 3/1995 | North, Jr. et al. | |
| 5,428,451 A | 6/1995 | Lea et al. | |
| 5,506,141 A | 4/1996 | Weinreb et al. | |
| 5,627,045 A | 5/1997 | Bochner et al. | |
| 5,854,684 A | 12/1998 | Stabile et al. | |
| 5,869,673 A * | 2/1999 | Tung et al. | 546/172 |
| 5,905,031 A | 5/1999 | Kuylen et al. | |
| 5,952,347 A * | 9/1999 | Arison et al. | 514/311 |
| 6,046,426 A | 4/2000 | Jeantette et al. | |
| 6,066,285 A | 5/2000 | Kumar | |
| 6,103,479 A | 8/2000 | Taylor | |
| 6,117,612 A | 9/2000 | Halloran et al. | |
| 6,206,672 B1 | 3/2001 | Grenda | |
| 6,224,907 B1 | 5/2001 | Davar et al. | |
| 6,228,437 B1 | 5/2001 | Schmidt | |
| 6,238,614 B1 | 5/2001 | Yang et al. | |
| 6,329,195 B1 | 12/2001 | Pfaller | |
| 6,333,192 B1 | 12/2001 | Petitte et al. | |
| 6,338,964 B1 | 1/2002 | Matanguihan et al. | |
| 6,342,384 B1 | 1/2002 | Chung et al. | |
| 6,344,354 B1 | 2/2002 | Webster et al. | |
| 6,372,494 B1 | 4/2002 | Naughton et al. | |
| 6,376,148 B1 | 4/2002 | Liu et al. | |
| 6,377,721 B1 | 4/2002 | Walt et al. | |
| 6,378,527 B1 | 4/2002 | Hungerford et al. | |
| 6,383,810 B2 | 5/2002 | Fike et al. | |
| 6,403,369 B1 | 6/2002 | Wood | |
| 6,410,309 B1 | 6/2002 | Barbera-Guillem et al. | |
| 6,413,744 B1 | 7/2002 | Morris et al. | |
| 6,413,746 B1 | 7/2002 | Field | |
| 6,455,310 B1 | 9/2002 | Barbera-Guillem et al. | |
| 6,465,000 B1 | 10/2002 | Kim | |
| 6,465,205 B2 | 10/2002 | Hicks, Jr. | |
| 6,468,788 B1 | 10/2002 | Marotzki | |
| 6,479,252 B1 | 11/2002 | Barbera-Guillem et al. | |
| 6,489,144 B1 | 12/2002 | Lau | |
| 6,492,148 B1 | 12/2002 | van Loon et al. | |
| 6,492,163 B1 | 12/2002 | Yoo et al. | |
| 6,506,598 B1 | 1/2003 | Andersen et al. | |
| 6,511,430 B1 | 1/2003 | Sherar et al. | |
| 6,528,286 B1 | 3/2003 | Ryll | |
| 6,569,422 B1 | 5/2003 | van Loon et al. | |
| 6,588,586 B2 | 7/2003 | Abasolo et al. | |
| 6,589,765 B1 | 7/2003 | Choi et al. | |
| 6,593,140 B1 | 7/2003 | Field | |
| 6,610,516 B1 | 8/2003 | Andersen et al. | |
| 6,627,426 B2 | 9/2003 | Biddle et al. | |
| 6,635,448 B2 | 10/2003 | Bucciarelli et al. | |
| 6,642,050 B1 | 11/2003 | Goto et al. | |
| 6,645,757 B1 | 11/2003 | Okandan et al. | |
| 6,649,408 B2 | 11/2003 | Bailey et al. | |
| 6,667,034 B2 | 12/2003 | Palsson et al. | |
| 6,670,180 B2 | 12/2003 | Block | |
| 6,670,184 B2 | 12/2003 | Chiarello et al. | |
| 6,673,591 B2 | 1/2004 | Lau | |

(Continued)

FOREIGN PATENT DOCUMENTS

EP 0508969 10/1992

(Continued)

OTHER PUBLICATIONS

Turek et al. "Leucine Aminopeptidase Activity by Flow Cytometry", Methods Cell Biol., 41(Chap.30): 461-468, 1994.

(Continued)

Primary Examiner—D. Margaret Seaman

(57) ABSTRACT

An amorphous form of montelukast sodium and a montelukast sodium lactose co-precipitate, processes for producing same, pharmaceutical compositions containing same and methods of treatment utilizing same are disclosed.

61 Claims, 5 Drawing Sheets

U.S. PATENT DOCUMENTS

| | | | |
|---|---|---|---|
| 6,686,190 | B2 | 2/2004 | Lau |
| 6,689,594 | B1 | 2/2004 | Hänni et al. |
| 6,692,961 | B1 | 2/2004 | Judd et al. |
| 2002/0151562 | A1* | 10/2002 | Seligman ............... 514/311 |
| 2002/0173033 | A1 | 11/2002 | Hammerick et al. |
| 2003/0015194 | A1* | 1/2003 | Schiewe et al. ........ 128/203.15 |
| 2003/0030184 | A1 | 2/2003 | Kim et al. |
| 2003/0032204 | A1 | 2/2003 | Walt et al. |
| 2003/0189850 | A1 | 10/2003 | Sasaki et al. |
| 2003/0211458 | A1 | 11/2003 | Sunray et al. |
| 2004/0235143 | A1 | 11/2004 | Sasaki et al. |
| 2005/0014201 | A1 | 1/2005 | Deutsch |
| 2005/0064524 | A1 | 3/2005 | Deutsch et al. |
| 2005/0187245 | A1 | 8/2005 | Alnabari et al. |

FOREIGN PATENT DOCUMENTS

| | | |
|---|---|---|
| EP | 480717 | 9/1998 |
| WO | WO 95/18107 | 6/1995 |
| WO | WO 98/15356 | 4/1998 |
| WO | WO 98/35223 | 8/1998 |
| WO | WO 99/45357 | 9/1999 |
| WO | WO 99/47922 | 9/1999 |
| WO | WO 01/35071 | 5/2001 |
| WO | WO 02/26114 | 4/2002 |
| WO | WO 02/063034 | 8/2002 |
| WO | WO 03/035824 | 1/2003 |
| WO | WO 03/011451 | 2/2003 |
| WO | WO 03/056330 | 7/2003 |
| WO | 03/066598 * | 8/2003 |
| WO | WO 03/066598 | 8/2003 |
| WO | WO 2004/077009 | 9/2004 |
| WO | WO 2004/108679 | 12/2004 |
| WO | WO 2004/113492 | 12/2004 |
| WO | WO 2005/007796 | 1/2005 |
| WO | WO 2005/011595 | 2/2005 |
| WO | WO 2005/040123 | 5/2005 |
| WO | WO 2005/074893 | 8/2005 |

OTHER PUBLICATIONS

Watson et al. "Enzyme Kinetics", Methods Cell Biol., 41:469-508, 1994.
Bedner et al. "Enzyme Kinetic Reactions and Fluorochrome Uptake Rates Measured in Individual Cells by Laser Scanning Cytometry", Cytometry, 33(1): 1-9, 1998. Abstract, p. 2, col. 1, §4-col. 2, §1, p. 8, col. 2, §2.
Sunray et al. "Cell Activation Influences Cell Staining Kinetics", Spectrochimica Part A, 53: 1645-1653, 1997.
Eisenthal et al. "Infection of K562 Cells With Influenza A Virus Increases Their Susceptibility to Natural Killer Lysis", Pathobiology, 65: 331-340, 1997.
Deutsch et al. "Apparatus for High-Precision Repetitive Sequential Optical Measurement of Living Cells", Cytometry, 16:214-226, 1994.
Sunray et al., "Determination of the Michaelis-Menten Constant (Km) of Intracellular Enzymatic Reaction for Individual Live Lymphocytes", Cytometry Supplement, 10: 68-69, & The XX Congress of the International Society for Analytical Cytology, Montpellier, F, 2000.
Darzynkiewicz et al. "Laser-Scanning Cytometry: A New Instrumentation With Many Applications", Experimental Cell Research, 249(1): 1-12, 1999. Abstract, p. 2, col. 2, §4-p. 4, col. 2, §2, p. 8, col. 1, §1-col. 2, §2.
Sunray et al. "The Trace and Subgrouping of Lymphocyte Activation by Dynamic Fluorescence Intensity and Polarization Measurements", Biochemical and Biophysical Research Communications, 261(3): 712-719, 1999. Abstract, p. 713, col. 1, §5, col. 2, §7-p. 714, col. 2, §1.
Sunray et al. "Determination of Individual Cell Michaelis-Menten Constants", Cytometry, 47(1): 8-16, 2002.
Dive et al. Cytometry Journal of Society for Analytical Cytology, 8(6): 552-561, 1987, Abstract.
Koh et al. "Poly(Ethylene Glycol) Hydrogel Microstructures Encapsualting Living Cells", Langmuir, 18(7): 2459-2462, 2002.
Lansing Taylor et al. "Real-Time Molecular and Cellular Analysis: The New Frontier of Drug Discovery", Current Opinion in Biotechnology, 12: 75-81, 2001.
Aplin et al. "Protein-Derivatised Glass Coverslips for the Study of Cell-to-Substratum Adhesion", Analytical Biochemistry, 113: 144-148, 1981.
Burlage et al. "Living Biosensors for the Management and Manipulation of Microbial Consortia",Annual. Rev. Microbiol., 48: 291-309, 1994.
Mrksich et al. "Using Self-Assembled Monolayers to Understand the Interactions of Man-Made Surfaces With Proteins and Cells", Annular Reviews in Biophysics and Biomolecular Structure, 25: 55-78, 1996.
Singhvi et al. "Engineering Cell Shape and Function", Science, 264: 696-698, 1994.
Riedel et al., "Arxula Adeninivorans Based Sensor for the Estimation of Bod", Analytical Letters, 31(1): 1-12, 1998.
Simonian et al., "Microbial Biosensors Based on Potentiometric Detection", Methods in Biotechnology,6, chapter 17: 237-248, 1998.
Arikawa et al., "Microbial Biosensors Based on Respiratory Inhibition", Methos in Biotechnology,6, chapter 16: 225-235, 1998.
Konno "Physical and Chemical Changes of Medicinals inMixtures withAdsorbents in the Solid State. IV. Study on reduced-Pressure Mixing for Practical Use ofAmorphous Mixtures of Flufenamic Acid", Chemical Pharmaceutical Bulletin, 38(7), 2003-2007, 1990.
Grant "Theory and Origin of Polymorphism", p. 1-33.
Morris et al. "Theoretical Approaches to Physical Transformations of Active Pharmaceutical Ingredients during Manufacturing processes", Advanced Drug Delivery Reviews 48: 91-114, 2001.
Brittain et al. "Effects of Pharmaceutical Processing on Drug Polymorphs and Solvates",p. 331-361.
Brittain et al. "Effects of Polymorphism and Solid-State Solvation on Solubility and Dissolution Rate", p. 278-305.
Dolbeare "Fluorescent Staining of Enzymes for Flow Cytometry", Methods Cell Biol., 33(Chap.8): 81-88, 1990.
Klingel et al. "Flow Cytometric Determination of Serine Proteinase Activities in Living Cells With Rhodamine 110 Substrates", Methods Cell Biol., 41(Chap.29): 449-460, 1994.
Malin-Berdel et al. "Flow Cytometric Determination of Esterase and Phosphatase Activities and Kinetics in Hemapoietic Cells With Fluorogenic Substrates", Cytometry, 1(3):222-228, 1980.
Nooter et al. "On-Line Flow Cytometry. A Versatile Method for Kinetic Measurement", Methods Cell Biol., 41(Chap.32): 509-526, 1994.
Yu et al. "Amorphous Pharmaceutical Solids: Preparation, Characterization and Stabilization", Advanced Drug Delivery Reviews, 48: 27-42, 2001. Abstract.
Notice of Allowance Dated May 28, 2008 From the U.S. Patent Office Re.: U.S. Appl. No. 11/048,746.
Official Action Dated Sep. 8, 2008 From the U.S. Patent Office Re.: U.S. Appl. No. 11/048,746.
Official Action Dated Sep. 28, 2007 From the U.S. Patent Office Re.: U.S. Appl. No. 11/048,746.
Brittain et al. "Effects of Pharmaccutical Processing on Drug Polymorphs and Solvates", p. 331-361., 1999.
Brittain et al. "Effects of Polymorphism and Solid-State Solvation on Solubility and Dissolution Rate", p. 278-305., 1999.
Grant "Theory and Origin of Polymorphism", Polymorphism in Pharmaceutical Solids, Chap. 1: 1-33, 1999.
Konno "Physical and Chemical Changes of Medicinals in Mixtures With Adsorbents in the Solid State. IV. Study on Reduced-Pressure Mixing for Practical Use of Amorphous Mixtures of Flufenamic Acid", Chemical Pharmaceutical Bulletin, 38(7): 2003-2007, 1990.
Morris et al. "Theoretical Approaches to Physical Transformations of Active Pharmaceutical Ingredients during Manufacturing processes", Advanced Drug Delivery Reviews 48: 91 114, 2001.

* cited by examiner

STABLE AMORPHOUS FORMS OF MONTELUKAST SODIUM

This application claims the benefit of priority from U.S. provisional patent application No. 60/541,052, filed on Feb. 3, 2004.

FIELD AND BACKGROUND OF THE INVENTION

The press invention relates to stable amorphous forms of montelukast sodium and, more particularly, to stable amorphous forms of montelukast sodium which are suitable for use in the preparation of solid dosage formulations, to processes of preparing same, to compositions containing the same and to methods of treatment using the same.

(R-(E)-1-(((1-(3-(2-(7-chloro-2-quinolinyl)ethenyl)phenyl)-3-(2-(1-hydroxy-1-methylethyl)phenyl)propyl)thio)methyl)cyclopropaneacetic acid sodium salt, also known by the name montelukast sodium, is represented by Formula I below:

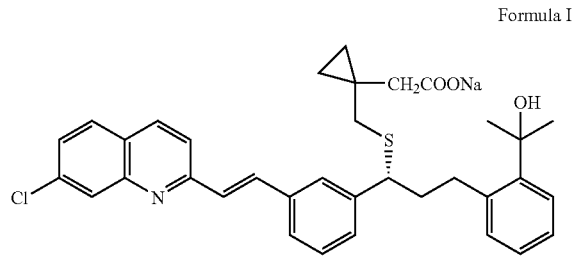

Formula I

Montelukast is freely soluble in ethanol, methanol and water but is practically insoluble in acetonitrile.

Montelukast sodium is a leukotriene antagonist, and is thus useful as an anti-asthmatic, anti-allergic, ant-inflammatory and cytoprotective agent. Montelukast sodium is currently indicated for the treatment of allergic rhinitis and asthma.

Montelukast sodium, formulated as tablets (containing 10.4 mg montelukast sodium), chewable tablets (containing 4.2 or 5.2 mg montelukast sodium) or oral granules (in a packet containing 4.2 mg montelukast sodium), is typically given once daily to the patients for the treatment of asthma and seasonal allergic rhinitis. Montelukast sodium is marketed in the United States and other countries by Merck & Co., Inc. under the trade name Singulair®.

However, the form of montelukast sodium used in preparing Singulair® is hygroscopic and therefore require special care in handling and storage, which adversely affect the efficiency of the production process.

Montelukast sodium and related compounds were first disclosed in European Patent No. EP 480,717. The synthesis of montelukast sodium, as taught in EP 480,717, involves coupling methyl 1-(mercaptomethyl)cyclopropaneacetate with (S)-1-(3-(2-(7-chloro-2-quinolinyl)ethyl(phenyl)-3-(2-(1-hydroxy-1-methylethyl)phenyl)propyl-methanesulfonate, followed by hydrolysis of the resulting methyl ester so as to form a free acid, which is followed by conversion of the free acid to a corresponding sodium salt. The sodium salt is prepared in an aqueous solution and the water is removed by freeze-drying.

International Patent Application published as WO 95/18107 teaches a method for the preparation of crystalline montelukast sodium, which involves the preparation of the dilithium dianion of 1-(mercaptomethyl) cyclopropaneacetic acid as an intermediate, followed by condensation thereof with 2-(2-(3-(S)-(3-(7-chloro-2-quinolinyl)ethenyl)phenyl)-3-methanesulfonyloxypropyl)phenyl)-2-propanol, to yield montelukast acid. The resulting montelukast acid is converted, via the corresponding dicyclohexyl amine salt, to montelukast sodium. The montelukast sodium is crystallized from a toluene/acetonitrile solution to obtain crystalline montelukast sodium. This publication further notes that the compounds disclosed in EP 480,717 are hydrated amorphous montelukast sodium, and are therefore not ideal for use in the formulation of pharmaceutical compositions.

International Patent Application PCT/US03/03700, published as WO 03/066598, discloses an anhydrous amorphous form of montelukast sodium. The amorphous montelukast sodium is prepared, according to the teachings of WO 03/066598, by providing a solution of montelukast free acid in an aromatic solvent; converting the free acid to an alkali salt using methanolic sodium hydroxide; adding a hydrocarbon solvent, and isolating the thus obtained amorphous montelukast sodium. Preparing amorphous montelukast sodium by flocculation from aromatic and hydrocarbon solvents is disadvantageous, particularly when compared to aqueous solutions, due to the toxicity, cost and typical hazardousness of such organic solvents.

In recent years, solid-state properties of drugs received a great focus in the pharmaceutical industry, as a major contributing factor to both bioavailability and formulation characteristics. The ability of some substances to exist in more than one form, whether crystalline or amorphous, was accredited as one of the most important solid-state property of drugs. While different chemical forms have the same chemical composition, they differ in the packing and geometrical arrangement thereof, and exhibit different physical properties such as melting point, shape, color, density, hardness, deformability, stability, dissolution, and the like.

General background and theory of forms is found for example in "Effects of Polymorphism and Solid-State Solvation on Solubility and Dissolution Rate", in Polymorphism in Pharmaceutical Solids, edited by Harry G. Brittain, Drugs and the Pharmaceutical Sciences, Volume 95, MARCEL DEKKER, Inc.; "Effects of Pharmaceutical Processing on Drug Polymorphs and Solvates", in Polymorphism in Pharmaceutical Solids, edited by Harry G. Brittain; Drugs and the Pharmaceutical Sciences, Volume 95, MARCEL DEKKER, Inc.; "Theoretical approaches to physical transformations of active pharmaceutical ingredients during manufacturing process", Morris et al, Advanced drug delivery reviews, 48, 2001; and Theory and Origin of Polymorphism in "Polymorphism in Pharmaceutical Solids" (1999) ISBN: 8247-0237.

In some cases, different forms of the same drug can exhibit very different solubility, and therefore different dissolution rates (release profile) in-vivo. It is known, for example, that amorphous forms of some drugs exhibit dissolution characteristics and bioavailability patterns different from corresponding crystalline forms [Konne T., Chem. Pharm. Bull., 38, 2003 1990]. For some therapeutic indications one bioavailability pattern may be favored over another. This phenomenon may be used to create better drugs that dissolve either rapidly or very slowly, according to the specific needs of each formulation. However, any failure to predict the bioavailability of a drug may result in administration of either too small or too large undesired doses, which may be dangerous to patients and in extreme cases, lethal.

Other examples are known, where different forms behave differently during physical processing like milling and pressing. Many process-induced solid-solid transitions of substances are known, that lead to either other crystalline forms or an amorphous form of the substance. The solid-state experts are in a constant search for forms that can withstand physical stress and still retain their original properties.

Different forms of a pharmaceutically useful compound therefore provide opportunities to improve the performance characteristics of a pharmaceutical product. Different forms enlarge the repertoire of materials that a formulation scientist has available for designing, for example, a pharmaceutical dosage form of an active pharmaceutical ingredient with a desired characteristic. It is well known that new forms of known useful compounds are of utility. Consequently, there is an ongoing search for new forms of known compounds used in pharmaceutical compositions, which may provide for improved performance thereof.

Hence, the prior art teaches hydrated amorphous montelukast sodium, (European Patent No. EP 480,717), which is highly hygroscopic and therefore its usage in solid formulations is inefficient. The prior art further teaches other forms of montelukast sodium, which were aimed at overcoming the limitations associated with the hydrated amorphous montelukast sodium disclosed in EP 480,717. These include, for example, crystalline montelukast sodium and anhydrous amorphous montelukast sodium (as taught in WO 95/18107 and WO 03/066598, respectively). As discussed hereinabove, formulating crystalline forms of substances into pharmaceutical compositions is limited by the instability of the crystalline form during the formulation process (e.g., when high pressure is applied), solubility characteristics of the substance, and other characteristics. As is further discussed hereinabove, the preparation of the anhydrous amorphous montelukast sodium taught in WO 03/066598 involves solvents such as aromatic hydrocarbons, aliphatic and alicyclic hydrocarbons and halogenated hydrocarbons, which are all considered disadvantageous when used in the preparation of medicaments, since they are relatively toxic, cost-inefficient and environmental unfriendly.

There is thus a widely recognized need for, and it would be highly advantageous to have, novel forms of montelukast sodium and improved processes for the preparation thereof, devoid of the above limitations.

SUMMARY OF THE INVENTION

Thus, the present invention provides novel amorphous forms of montelukast sodium, and processes for the preparation thereof.

The general techniques that may lead to the discovery of amorphous form of a certain compound are well known to those who are skilled in the art. Those who are skilled in the art appreciate that in a search for amorphous forms of a certain compound, any one of these techniques is expected to fail. The search is an empirical exercise that involves series of trial and error experiments with different techniques and conditions. For these reasons, it is impossible to predict the experimental conditions that will produce an amorphous form of montelukast sodium, what the properties of such a form are and whether such a form will be suitable for use in the preparation of a pharmaceutical preparation. It is, however, possible to provide methods that have successfully and selectively produced montelukast sodium after conducting a series of trial and error experiments.

Herein novel amorphous forms of montelukast sodium that are suitable for pharmaceutical use are presented.

According to the teachings of the present invention there is provided stable, non-hygroscopic, amorphous montelukast sodium.

Further according to the teachings of the present invention there is also provided a co-precipitate of amorphous montelukast sodium and at least one pharmaceutically acceptable excipient. In an embodiment of this aspect of the present invention, the at least one pharmaceutically acceptable excipient comprises lactose. In another embodiment, the ratio between the amorphous montelukast sodium and lactose ranges between about 1:0.1 and about 1:10, preferably the ratio ranges between about 1:0.5 and 1:2, and even more preferably the ratio is about 1:1.

The amorphous montelukast sodium of the present invention and the co-precipitate including same are non-hygroscopic. In an embodiment of the present invention, upon exposure to an atmosphere of about 30% humidity for a period of about one hour, a weight gain of the amorphous montelukast sodium or the co-precipitate is less than 2 weight percents of the total weight thereof, preferably less than 0.5 weight percents.

The amorphous montelukast sodium of the present invention and the co-precipitate including same are stable. In an embodiment of the present invention the amorphous montelukast sodium retains an amorphous character subsequent to storage at a temperature of at least 25° C. for a time period of at least 2 months and even subsequent to storage at a temperature of about 40° C. for a time period of about 3 months.

In an embodiment of the present invention the amorphous montelukast sodium retains an amorphous character subsequent to application of a pressure greater than 5000 Kg/cm$^3$ for a period of about one minute and even subsequent to application of pressure of about 10000 Kg/cm$^3$ for a period of about one minute.

Both the amorphous montelukast sodium of the present invention and the co-precipitate including same have properties advantageous for use in preparing pharmaceutical compositions therewith. In an embodiment of the present invention, the amorphous montelukast sodium, as well as the co-precipitate including same, have a bulk density that ranges between about 0.10 gram/cm$^3$ and about 0.40 gram/cm$^3$ g/cm$^3$, preferably greeter than 0.10 g/cm$^3$ or even greater than 0.20 g/cm$^3$.

In an embodiment of the present the amorphous montelukast sodium of the preset invention has a powder X-ray diffraction pattern substantially as depicted in FIG. 2.

In another embodiment of the present invention an exemplary co-precipitate which comprises the amorphous montelukast sodium and lactose has a powder X-ray diffraction patter substantially as depicted in FIGS. 3, 4 and 5.

According to the teaching of the present invention there is also provided a process of preparing the amorphous montelukast sodium of the present invention described above, the process comprises dissolving montelukast sodium in a solvent, to thereby provide a solution of montelukast sodium in the solvent and removing the solvent from the solution by spray dying. In an embodiment of this aspect of the present invention, the solvent is selected from the group consisting of water, a water miscible organic solvent and a combination thereof. In another embodiment of this aspect of the present invention, the water miscible organic solvent is selected from the group consisting of acetone, a $C_1$-$C_3$ alcohol, and any combination thereof, preferably ethanol. In preferred embodiments of this aspect of the preset invention the solvent is water, ethanol or a mixture of water and ethanol.

According to the teachings of the present invention there is also provided a process of preparing the co-precipitate of the present invention, the process comprising dissolving montelukast sodium and at least one pharmaceutically acceptable excipient in a solvent, to thereby provide a solution of montelukast sodium in the solvent and removing the solvent from the solution, thereby obtaining the co-precipitate of amorphous montelukast sodium and the at least one excipient. In an embodiment of this aspect of the present invention, the at least one pharmaceutically acceptable excipient is lactose. In another embodiment of this aspect of the present invention, the at least one pharmaceutically acceptable excipient is lactose monohydrate. In an embodiment of the co-precipitate of the present invention, the ratio between the amorphous montelukast and lactose ranges between about 1:0.1 and about 1:10, preferably the ratio ranges between about 1:0.5 and 1:2, and even more preferably the ratio is about 1:1.

In an embodiment of this aspect of the present invention, removing the solvent is effected by freeze drying the solution.

In an embodiment of this aspect of the present invention, removing the solvent is effected by spray drying the solution.

In an embodiment of the present invention, the solvent is selected from the group consisting of water, a water miscible organic solvent and a combination thereof. In an embodiment of the present invention, the water miscible organic solvent is selected from the group consisting of acetone, a $C_1$-$C_3$ alcohol, and any combination thereof, preferably ethanol. In preferred embodiments of the present invention, the solvent is water, ethanol or a mixture of water and ethanol.

According to the teachings of the present invention there are also provided pharmaceutical compositions, comprising the amorphous montelukast sodium of the present invention and/or the co-precipitate according to the present invention, and a pharmaceutically actable carrier. In an embodiment of this aspect of the present invention, the pharmaceutical composition is formulated in a solid dosage form, including but not limited to a tablet, a capsule, a peel, a dragee, a powder and granules. In another embodiment of this aspect of the present invention, the pharmaceutical composition of the present invention is packaged in a packaging material and identified in print, in or on said packaging material, for use for a need selected from the group consisting of curing a condition, treating a condition, preventing a condition, treating symptoms of a condition, curing symptoms of a condition, ameliorating symptoms of a condition, treating effects of a condition, ameliorating effects of a condition, and preventing results of a condition in which treatment with montelukast sodium is beneficial. Exemplary conditions include but are not limited to allergic rhinitis and asthma According to the teachings of the present invention there is provided a method of treating a medical condition in which administration of montelukast sodium is beneficial, the method comprising administering to a subject in need thereof a therapeutically effective amount of one or more of the pharmaceutical compositions of the present invention. Exemplary conditions include but are not limited to allergic rhinitis and asthma. In an embodiment of the present invention, administration of the pharmaceutical composition is preferably administered orally. Preferably, the pharmaceutical composition is formulated in a solid dosage form.

As used herein, the terms "comprising" and "including" or grammatical variants thereof are to be taken as specifying the stated features, integers, steps or components but do not preclude the addition of one or more additional features, integers, steps, components or groups thereof. These terms encompass the terms "consisting of" and "consisting essentially of".

The phrase "consisting essentially of" or grammatical variants thereof when used herein are to be taken as specifying the stated features, integers, steps or components but do not preclude the addition of one or more additional features, integers, step components or groups thereof but only if the additional features, integers, steps, components or groups thereof do not materially alter the basic and novel characteristics of the claimed composition, device or method.

The term "method" or "process" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. Implementation of the methods of the present invention involves performing or completing selected tasks or steps manually, automatically, or a combination thereof.

The term "active ingredient" refers to a pharmaceutical agent including any natural or synthetic chemical substance that subsequent to its application has, at the very least, at least one desired pharmaceutical or therapeutic effect.

The term "therapeutically effective amount" or "pharmaceutically effective amount" denotes that dose of an active ingredient or a composition comprising the active ingredient that will provide the therapeutic effect for which the active ingredient is indicated.

As used herein, the singular form "a," "an," and "the" include plural references unless the context clearly dictates otherwise. For example, the term "a compound" or "at least one compound" may include a plurality of compounds, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5 and. 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

BRIEF DESCRIPTION OF THE FIGURES

The invention is herein described, by way of example only, with reference to the accompanying drawings. With specific reference now to the drawing in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE EMBODIMENTS

Figure 1:
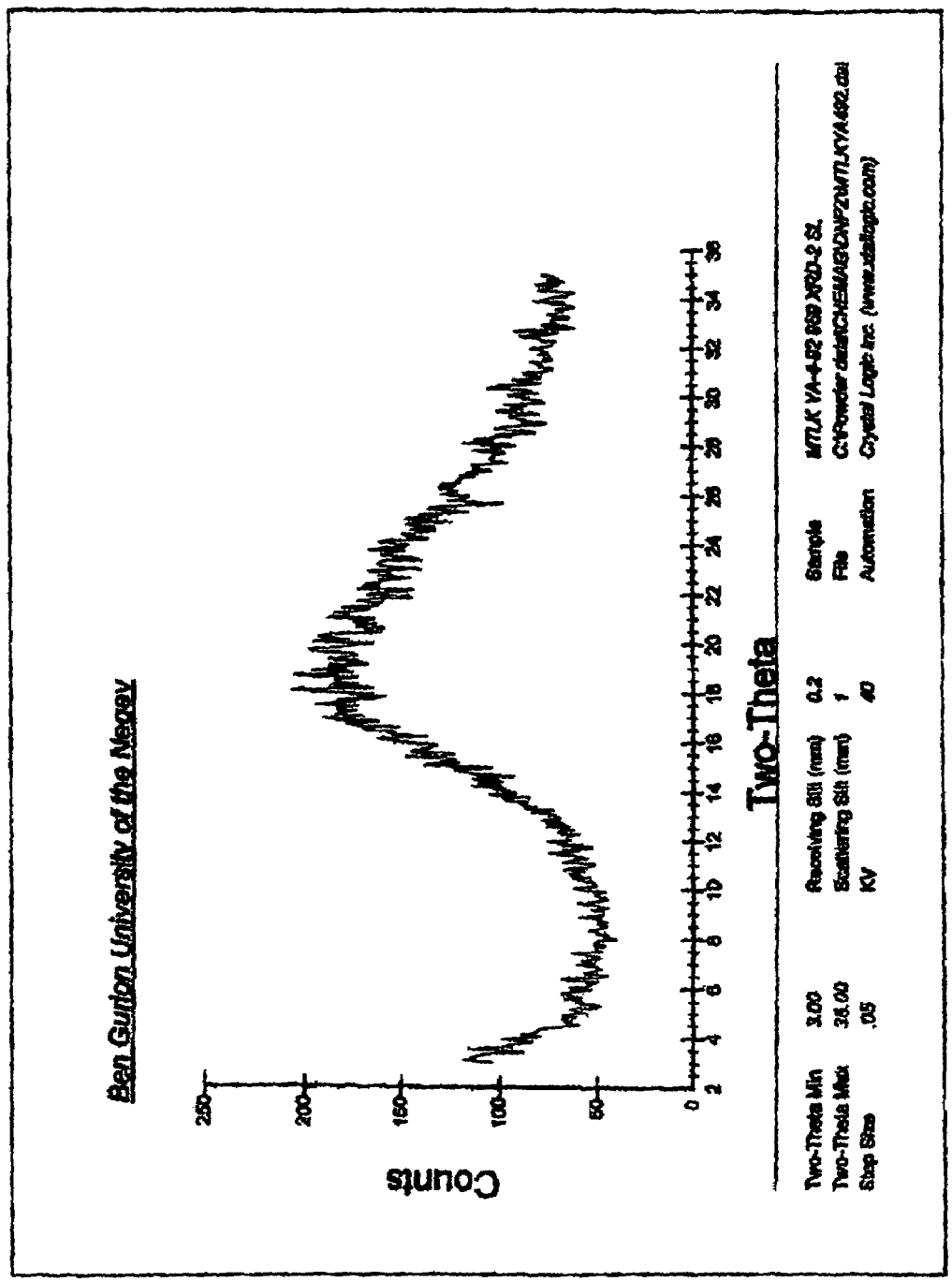
FIG. 1 presents an X-ray powder diffractogram of exemplary amorphous montelukast sodium prepared by freeze-drying according to the process described in European Patent No. EP 480,717.

The amorphous form of montelukast sodium of the present invention as well as processes of preparing same, pharmaceutical compositions including same and methods of treatment using same are described hereinbelow. The co-precipitates of amorphous montelukast sodium of the present invention as well as processes preparing same, pharmaceutical compositions including same and methods of treatment using same are further described hereinbelow.

The principles, uses and implementations of the teachings of the present invention may be better understood with reference to the accompanying description and figures. Upon perusal of the description and figures present herein, one skilled in the art is able to implement the teachings of the present invention without undue effort or experimentation.

Before explaining at least one embodiment of the invention in detail, it is to be understood that the invention is not limited in its application to the deals set forth herein. The invention can be implemented with other embodiments and can be practiced or carried out in various ways. It is also understood that the phraseology and terminology employed herein is for descriptive purpose should not be regarded as limiting.

Generally, the nomenclature used herein and the laboratory procedures utilized in the present invention include techniques from the fields of analytical chemistry, biology, chemistry, engineering and synthetic chemistry. Such techniques are thoroughly explained in the literature. Unless otherwise defined, all technical and scientific terms used herein have the same meaning as commonly understood by one of ordinary skill in the art to which the invention belongs. In addition, the descriptions, materials, methods and examples are illustrative only and not intended to be limiting. Methods and materials similar or equivalent to those described herein can be used in the practice or testing of the present invention. All publications, patent applications, patents and other references mentioned are incorporated by reference in their entirety as if fully set forth herein. In case of conflict, the specification herein, including definitions, will control.

As used herein, the term "amorphous" describes a solid devoid of long-range crystalline order.

The term "co-precipitate" describes a mixture of two or more solid substances (herein amorphous montelukast sodium and one or more pharmaceutically acceptable excipients) obtained by co-precipitation thereof from a solution.

The amorphous montelukast sodium and the co-precipitates including same described herein preferably contain less tan about 10% crystalline montelukast sodium, and more preferably are essentially free of crystalline montelukast sodium.

Herein, the phrase "essentially free of crystalline montelukast sodium" means that no crystalline montelukast sodium can be detected within the limits of a powder. X-ray Diffractometer comparable to the instrumentation described hereinbelow in the Experimental section.

The teachings of the present invention relate to two general types of substances. The first substance is stable, non-hygroscopic, amorphous montelukast sodium. The second substance is a co-precipitate of amorphous montelukast sodium and at less one pharmaceutically acceptable excipient.

As used herein, the phrase "pharmaceutically acceptable excipient" refers to an inert substance which is added so as to provide a pharmaceutical composition with a desired characteristic.

Examples, without limitation, of acceptable excipients typically used in pharmaceutical compositions include fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose, and/or physiologically acceptable polymers such as polyvinylpyrrolidone (PVP).

While the present invention is aimed at providing montelukast sodium that can be efficiently used in various formulations and particularly in solid dosage formulations, the pharmaceutically acceptable excipient in the co-precipitate of the present invention is preferably selected so as to improve the mechanical characteristics of montelukast sodium in terms of, e.g., mechanical stability, physical stability, bulk density and the like. An example of such an excipient is lactose. Lactose is known as an additive which upon being added to a solution of an amorphous substance, leads to the production of free-flowing powders. As is well known in the art, free-flowing powders are highly suitable for formulation processes.

Thus, an, exceptionally preferred co-precipitate according to the present invention is a co-precipitate of amorphous montelukast sodium with lactose. The ratio between the amorphous montelukast sodium and lactose preferably ranges between about 1:0.1 and about 1:10, more preferably between about 1:0.5 and 1:2 and more preferably is about 1:1.

As noted in the background section hereinabove, previously disclosed amorphous forms of montelukast sodium are hygroscopic and/or include potentially toxic organic solvents, making such forms unsuitable for use in the preparation of pharmaceutical compositions.

It has now been surprisingly found that preparing amorphous montelukast sodium by a process that involves spray drying from an aqueous solution provides a product with desired characteristics (e.g., stability, relatively high bulk density, and non-hygroscopicity). Further, it has been surprisingly found that preparing a co-precipitate of amorphous montelukast sodium with an excipient, from an aqueous solution, provides a product with such desired characteristics, whether prepared by spray dying or freeze drying.

Thus, the present inventors have now surprisingly uncovered amorphous montelukast sodium that is stable, not hygroscopic and, in addition, has a relatively high bulk density, and hence is exceptionally suitable for preparing pharmaceutical compositions. The present inventors have also uncovered a co-precipitate of amorphous montelukast sodium and one or more pharmaceutically acceptable excipient(s), especially a co-precipitate of amorphous montelukast sodium and lactose, which is exceptionally suitable for preparing pharmaceutical compositions by being stable, non-hygroscopic and having a relatively high bulk density.

As used herein, the term "stable" regarding the substances of the present invention is meant to define a characteristic of the substance by which the substance maintains chemical and physical features during storage or other challenging conditions, particularly those used in formulating procedures.

As is detailed hereinafter, the substances of the present invention were found to be highly stable, maintaining their amorphous character during e.g., storage and application of high pressure.

The term "non-hygroscopic" regarding the substances of the present invention is meant to define a characteristic of the substance by which the tendency of the substance to absorb water is negligible.

The amorphous montelukast sodium and the co-precipitates including same according to the preset invention are surprisingly non-hygroscopic. As is demonstrated in the Examples section that follows, upon exposure to an atmosphere of about 30% humidity for a period of one hour, the change in the total weight of exemplary substances according to the present invention was found to be about 0.36 weight percents. Hence, the amorphous montelukast sodium according to the present invention is characterized by such non-hygroscopicity that upon exposure to an atmosphere of about 30% humidity for a period of one hour, the weight gain thereof is preferably less than 2 weight percents, more preferably less than 1.5 weight percents, more preferably less than 1 weight percents, and even more preferably less than 0.5 weight percents. In one embodiment, the water content of an exemplary co-precipitate of amorphous montelukast sodium according to the present invention changed from about 3.75 weight percents to about 4.11 weight percents upon exposure to an atmosphere of about 30% humidity for a period of one hour.

This lack of hygroscopicity of the amorphous montelukast sodium and the co-precipitate thereof renders these substances exceptionally suitable for use in preparing pharmaceutical compositions.

The amorphous montelukast sodium and the co-precipitate thereof according to the present invention are further characterized by high stability. As is further demonstrated in the Examples section that follows, it is shown that the substances of the present invention retain an amorphous character while being stored for more than two months at a temperature higher than room temperature (e.g., of at least 25° C.). More specifically, it is shown that the substances of the present invention retain an amorphous character subsequent to storage at a temperature of about 40° C. for a time period of about 3 months. This stability of the amorphous montelukast sodium and the co-precipitates thereof renders these substances exceptionally suitable for use in paring pharmaceutical compositions.

An additional advantage of the substances of the present invention is that these substances retain an amorphous character under conditions typically used when preparing compressed solid dosage forms such as tablets. As is demonstrated in the Examples section that follows and the accompanying drawings, the amorphous montelukast sodium and an exemplary co-precipitate thereof according to the present invention retained the amorphous character subsequent to application of a high pressure, e.g., of about 10,000 kg/cm$^3$, for a period of about one minute, as is widely employed in solid dosage formulations.

The substances of the present invention are particularly advantageously characterized by a relatively high bulk density. Specifically, the amorphous montelukast sodium and the co-precipitates thereof according to the present invention have a bulk density grater than 0.1 gram/cm$^3$, such that preferably the amorphous montelukast sodium and the co-precipitates thereof according to the present invention have a bulk density that ranges from 0.1 gram/cm$^3$ to 0.4 gram/cm$^3$, and, more preferably, greater than about 0.2 gram/cm$^3$. Such a relatively high bulk density of the amorphous montelukast sodium and the co-precipitates thereof according to the present invention these substances exceptionally suitable for use in preparing pharmaceutical compositions.

As is clear to one skilled in the art, such bulk densities allow efficient mixing of the substance with solid carriers and other materials during formulation of a solid dosage form of a pharmaceutical composition. For comparison, the bulk density of an amorphous montelukast sodium prepared according to the prior art procedure described in European Patent No. EP 480,717 was found to be 0.061 gram/cm$^3$ (see, Reference Example 1 in the Examples section that follows), a bulk density that is too low for convenient use in the preparation of pharmaceutical compositions.

The advantageous characteristics of the amorphous montelukast sodium and the co-precipitate including the amorphous montelukast sodium and an excipient render these substances highly superior to the presently known forms of montelukast sodium.

Processes of Preparing Amorphous Montelukast Sodium and Co-precipitates Containing Same:

The amorphous montelukast sodium of the present invention is generally prepared by dissolving montelukast sodium in a solvent to thereby provide a solution of the montelukast sodium in the solvent and then removing the solvent from the solution by spray drying The co-precipitate of the present invention is generally prepared by dissolving montelukast sodium and one or more pharmaceutically acceptable excipients in a solvent to thereby provide a solution of the montelukast sodium and the excipient in the solvent and then removing the solvent from the solution, preferably by spray drying or freeze-drying.

As noted above, a preferred pragmatically acceptable excipient is lactose, preferably added to the solvent as lactose monohydrate. Depending on the embodiment, the weight ratio between the amorphous montelukast and lactose ranges between about 1:0.1 and about 1:10, preferably being about 1:1.

A first primed method of removing the solvent suitable for preparing the co-precipitate according to the present invention is by freeze-drying. In freeze drying the solution comprises water as a solvent. The solution is frozen using conditions that avoid precipitation and/or crystallization of substances in the solution. The frozen solution is then exposed to a reduced pressure so that the water sublimates from the frozen solution leaving an amorphous form of the substances to be gathered. The prior art method of preparing amorphous montelukast sodium using freeze-drying leads to a product having unsuitable physical properties.

A second preferred method of removing the solvent, suitable for preparing both amorphous montelukast and a co-precipitate of the present invention is by spray drying. In spray drying, a solution is sprayed from a nozzle into or with a large volume of a gas such as air. Generally, the solution, the nozzle and/or the gas are heated. The spraying from the nozzle generates droplets of solution containing substances in the solution. The combination of gas and heat causes the solvents in the droplets to evaporate, leaving an amorphous form of the substances to be gathered. Unpredictably and in contrast to the prior art amorphous montelukast sodium prepared by freeze-drying, the amorphous montelukast sodium of the present invention prepared by spray drying has a significantly higher bulk density than does the prior art amorphous montelukast sodium prepared by freeze-drying.

In embodiments of this aspect of the present invention, suitable solvents include but are not limited to water, water miscible organic solvents and combinations thereof. Suitable water miscible organic solvents include but are not limited to acetone, a $C_1$-$C_3$ alcohol (preferably ethanol), and any combination thereof.

In a preferred embodiment, the solvent is water. In another preferred embodiment the solvent is ethanol. In still another preferred embodiment of the present invention, the solvent is a mixture of water and ethanol, preferably in a 1:1 ratio.

In embodiments of this aspect of the present invention, when spray drying is used in a process of preparing a substance of the present invention, the temperature of the nozzle is greater than about 75° C., preferably between about 100° C. and about 180° C., more preferably between about 110° C. and about 170° C. and even more preferably between about 120° C. and about 160° C. Additional preferred conditions for spray drying are described in the Examples section that follows.

Pharmaceutical Compositions:

As noted above, the substances of the present invention are exceptionally suitable for use in pharmaceutical compositions of the present invention.

Similar to prior art Montelukast sodium forms, the substances of the present invention are generally useful for the preparation of pharmaceutical compositions where montelukast sodium is an active ingredient. The purpose of a pharmaceutical composition is to facilitate administration of a compound to a subject. The term "active ingredient" refers to a compound which is accountable for a biological effect of a pharmaceutical composition.

Generally a pharmaceutical composition according to the present invention includes at least one of the substances of the present invention (that is amorphous montelukast sodium as described above or a co-precipitate as described above), as an active ingredient, together with a pharmaceutically acceptable carrier.

The terms "physiologically acceptable carrier" and "pharmaceutically acceptable carrier", which may be used interchangeably, refer to a carrier or a diluent that does not cause significant irritation to an organism and does not abrogate the biological activity and properties of the administered compound.

A pharmaceutically acceptable carrier generally includes, in addition to the carrier or diluent, such components as antibacterial agents, antioxidant agents, binding agents, buffering agents, bulking agents, coloring agents, diluents, disintegrants, emulsifying agents, excipients, flavoring agents, glidants, lubricants, skin penetration enhancers, sweetening agents, viscosity modifying agents and any combination thereof which provide the composition with desired characteristics.

A pharmaceutical composition according to the present invention can include, in addition to one or more of the substances of the present invention, an additional form of montelukast sodium, and/or an additional active ingredient other than montelukast sodium.

A pharmaceutical composition of the present invention can be formulated in various forms. These include, without limitations, an aerosol, a bolus, a capsule, a cream, a delayed release capsule, a dispersion, a dissolvable powder, a dragee, drops, a gel capsule, granules, an injection, an inhalable form, a liposome, an ointment, a patch, a pill, a powder, a suppository, a suspension, a syrup, a tablet, a tincture, a topical cream and a troche.

Since at present montelukast sodium is preferably administered orally, preferred forms of a pharmaceutical composition according to the present invention include solid dosage form for oral administration such as, but not limited to, tablets (including chewable tablets), capsules, peels, dragees, powders and granules.

The pharmaceutical compositions according to the present invention may be manufactured by processes well known in the art, e.g., by means of conventional mixing, dissolving, granulating, dragee-making, levigaing, emulsifying, encapsulating, entrapping or lyophilizing processes.

Techniques for formulation and administration of compounds as medicaments may be found in "Remington's Pharmaceutical Sciences," Mack Publishing Co., Easton, Pa., latest edition, which is incorporated herein by reference.

Pharmaceutical compositions suitable for use in context of the present invention include compositions where the active ingredients are contained in an amount effective to achieve the intended purpose. More specifically, a therapeutically effective amount means an amount of active ingredient effective to cure a condition, treat a condition, prevent a condition, treat symptoms of a condition, cure symptoms of a condition, ameliorate symptoms of a condition, treat effects of a condition, ameliorate effects of a condition, and prevent results of a condition. The pharmaceutical compositions according to the present invention are particularly useful with regard to conditions in which treatment by Montelukast sodium is beneficial. Such conditions include, but are not limited to, allergic rhinitis, asthma, and any of the conditions listed hereinunder.

Hence, according to a preferred embodiment of the present invention, the pharmaceutical composition described above is packages in a packaging material and identified in print, in or on the packaging material for treating a medical condition as described herein.

Methods of Treatment:

A pharmaceutical composition of the present invention is useful in implementing the method of treating a medical condition in which administration of montelukast sodium is beneficial. The method is effected by administering to a subject in need thereof a therapeutically effective amount of the pharmaceutical composition of the present invention, as described hereinabove. Preferably, the administering is effected orally. Further preferably, the pharmaceutical composition is formulated in a solid dosage form, as is detailed hereinabove.

Medical conditions that are treatable by the compositions of the present invention include, without limitation: pulmonary disorders including diseases such as asthma, chronic bronchitis, and related obstructive airway diseases; allergies and allergic reactions such as allergic rhinitis, contact, allergic conjunctivitis, and the like; inflammation such as arthritis or inflammatory bowel disease; pain; skin disorders such as psoriasis, atopic eczema, and the like; conditions related to cardiovascular disorders such as angina, myocardial ischemia, hypertension, platelet aggregation and the like; renal insufficiency arising from ischmaemia induced by immunological or chemical (cyclosporin) etiology; migraine or cluster headache; ocular conditions including inflammatory diseases such as uveitis; hepatitis resulting from chemical, immunological or infectious stimuli; trauma or shock states such as burn injuries, endotoxemia and the like; allograft rejection; prevention of side effects associated with therapeutic administration of cytokines such as interleukin II and tumor necrosis factor; chronic lung diseases such as cystic fibrosis, bronchitis and other small and large-airway diseases; cholecystitis; and glomerular nephritis.

Additional conditions include, erosive gastritis; erosive esophagitis; diarrhea; cerebral spasm; premature labor; spontaneous abortion, dysmenorrhea' ischemia, noxious agent-induced damage of necrosis of hepatic, pancreatic, renal, or myocardial tissue; liver parenchymal damage caused by hepatodxix agents such is CC14 and D-galactosamine; ischaemic renal failure; disease-induced hepatic damage; bile salt induced pancreatic or gastric damage; trauma- or stress-induced cell damage; and glyceral-induced renal failure.

Additional objects, advantages, and novel features of the present invention will become apparent to one ordinarily skilled in the art upon examination of the following examples, which are not intended to be limiting. Additionally, each of the various embodiments and aspects the present invention as delineated hereinabove and as claimed in the claim section below finds experimental support in the following examples.

EXAMPLES

Reference is now made to the following examples, which together with the above description, illustrate the invention in a non limiting fashion.

Experimental Methods

The novel forms of montelukast sodium of the present invention have been characterized by powder X-ray diffraction, which produces a fingerprint of the particular form. Measurements of 2θ values typically are accurate within ±0.2 degrees 2θ.

X-ray diffraction data were acquired using a PHILIPS X-ray diffractometer model PW1050-70. System description: Kα1=1.54178 Å, voltage 40 kV, current 28 mA, diversion slit=1°, receiving slit=0.2 mm, scattering slit=1° with a Graphite monochromator. Experiment parameters: pattern measured between 2θ=4° and 2θ=30° with 0.05° increments; count time was 0.5 second per increment.

Mini spray dryer of Buchi 190 was used for spray drying.

Freeze-drying was performed with Virtis Advantage instrument.

Water content was measured using a Karl Fischer Titrator (Mettler Toledo Model DL-53) according to standard procedures.

Reference Example 1

Amorphous Montelukast Sodium

Amorphous montelukast sodium was prepared according to the process disclosed in European Patent No. EP 480,717. Thus, montelukast sodium (5.0 grams) was dissolved in water (200 ml) and filtered. The solution was then freeze dried (lyophilized), producing a residue with a bulk density of 0.061 gram/cm$^3$.

The X-ray analysis of the residue is presented in FIG. 1.

Example 1

Amorphous Montelukast Sodium

Montelukast sodium (5.0 grams) was stirred in ethanol (100 ml) in a round bottom flask until complete dissolution was achieved. The solution was then spray-dried, producing a residue with a bulk density of 0.269 gram/cm$^3$.

Spray drying parameters were: outlet temperature of approximately 85° C., airflow 30 m$^3$/h and solution feed rate of approximately 6 ml/minute.

The X-ray analysis of the residue gave a featureless diffractogram with a broad peak centered at 2θ about 22°, showing the residue was amorphous. The residue was pressed at 10,000 Kg/cm$^3$ for 1 minute.

Figure 2:
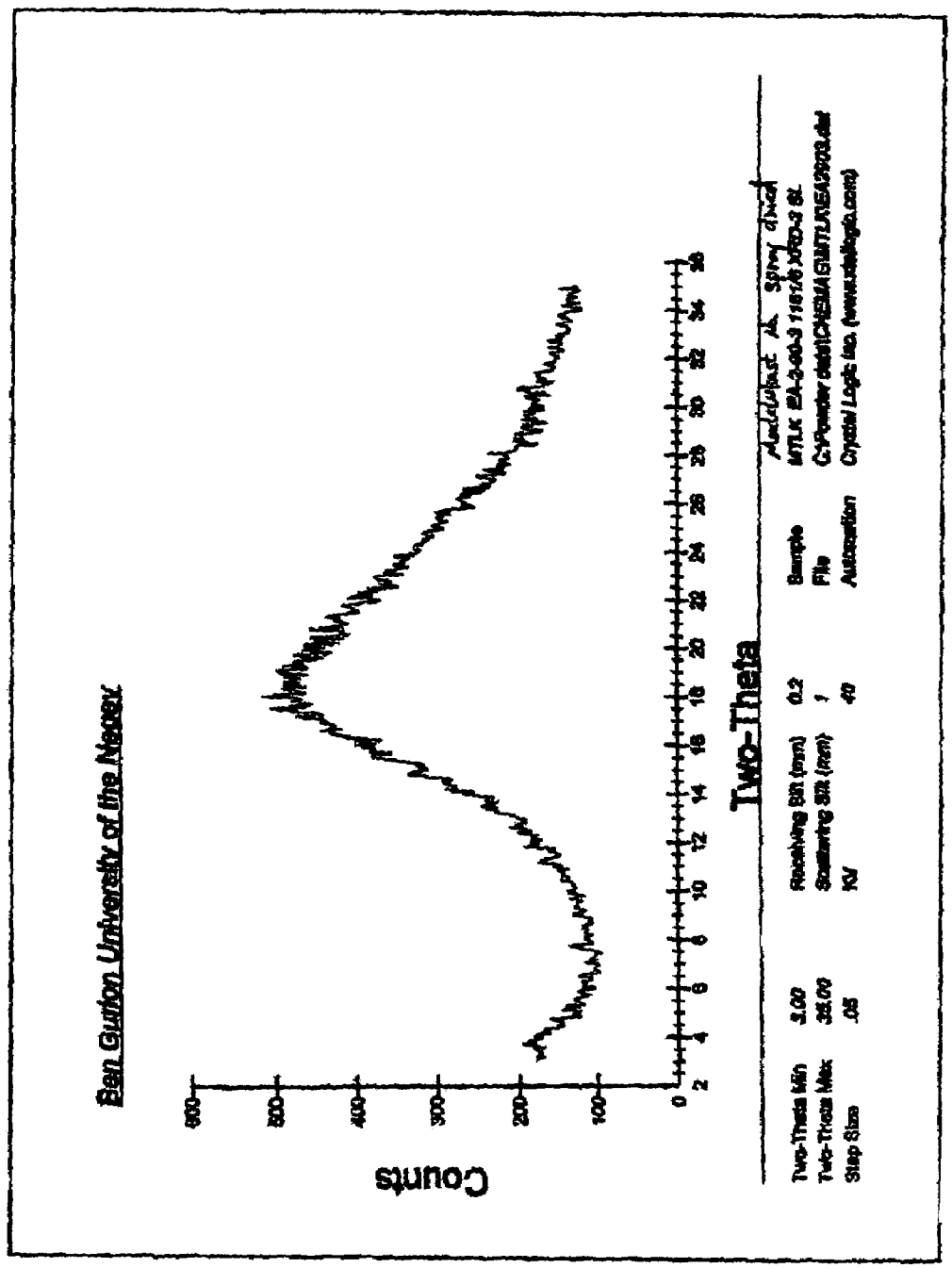
FIG. 2 presents an X-ray powder diffractogram of exemplary amorphous montelukast sodium according to the present invention, prepared by spray-drying and pressing at 10,000 Kg/cm$^3$ for 1 minute.

The X-ray analysis of the pressed residue obtained by pressing the residue at 10,000 Kg/cm3 for 1 minute gave a featureless diffractogram with a broad peak centered at 2θ about 22°, as shown in FIG. 2, indicating that the residue remained amorphous.

Example 2

Amorphous Mixture of Montelukast Sodium and Lactose

Montelukast sodium (2.5 grams) and lactose monohydrate (2.5 grams) were stirred in a 1:1 water/ethanol mixture (100 ml) in a round bottom flask until complete dissolution was achieved. The solution was then spray-dried, producing a residue which is a co-precipitate of the Montelukast sodium and the lactose.

Spray drying parameters were: outlet temperature of approximately 85° C., airflow 30 m$^3$/h and solution feed rate of approximately 5.8 ml/minute.

The X-ray analysis of the residue gave featureless diffractogram showing the residue was amorphous.

Figure 3:
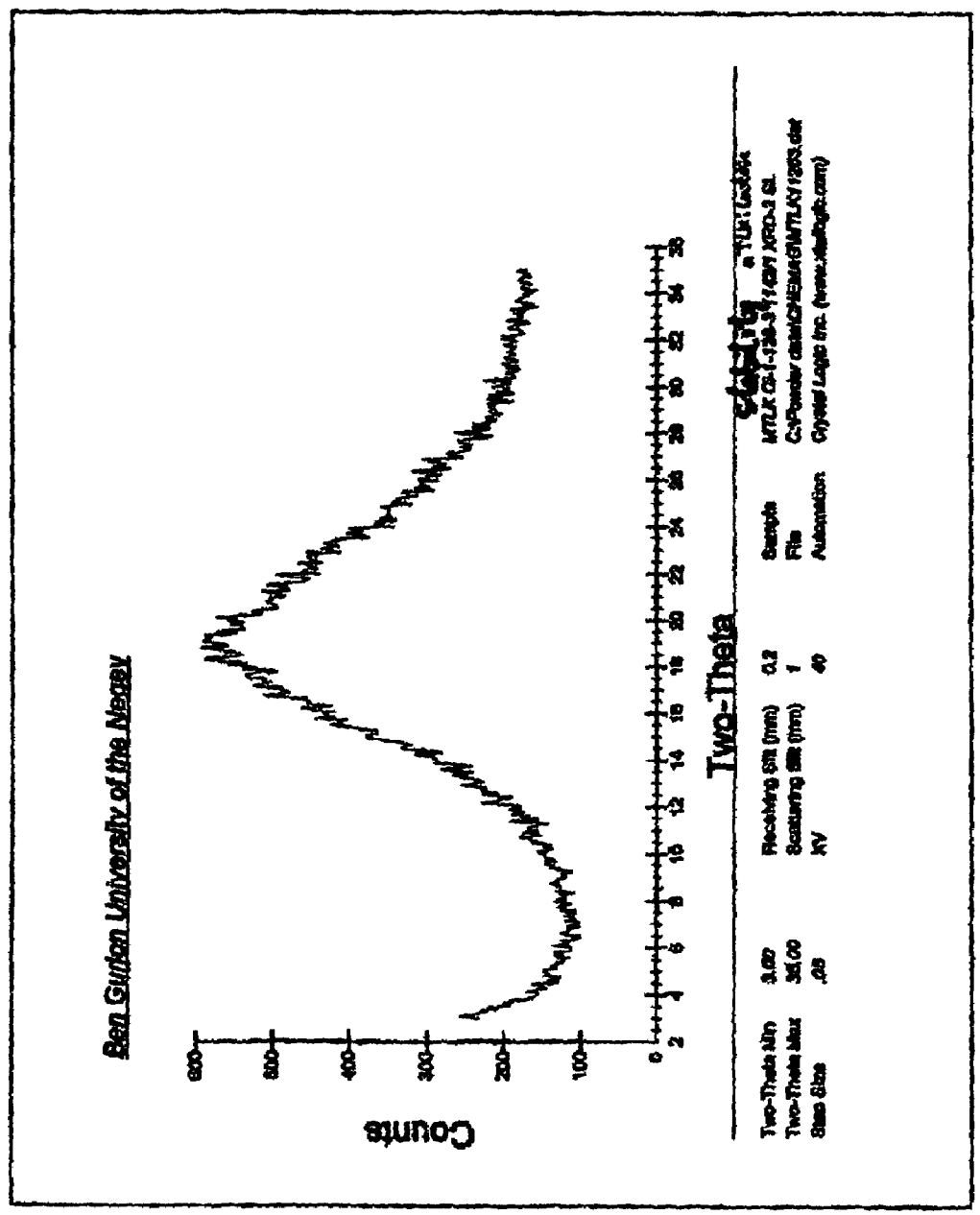
FIG. 3 presents an X-ray powder diffractogram of an exemplary co-precipitate of amorphous montelukast sodium and lactose according to the present invention, prepared by spray drying and stored at a temperature of 40° C. for three months.

The residue was stored for 3 months at a temperature of 40±2° C. The X-ray analysis of the stored residue gave a featureless diffractogram, as shown in FIG. 3, indicating that the residue remained amorphous.

Example 3

Amorphous Mixture of Montelukast Sodium and Lactose

Montelukast sodium (5.0 grams) and lactose monohydrate (0.5 gram) were dissolved in water (200 ml) and filtered. The solution was then lyophilized, producing a residue which is a co-precipitate of the Montelukast sodium and the lactose. The X-ray analysis of the residue gave a featureless diffractogram showing the residue was amorphous.

The residue was then pressed at 10,000 Kg/cm3 for 1 minute.

Figure 4:
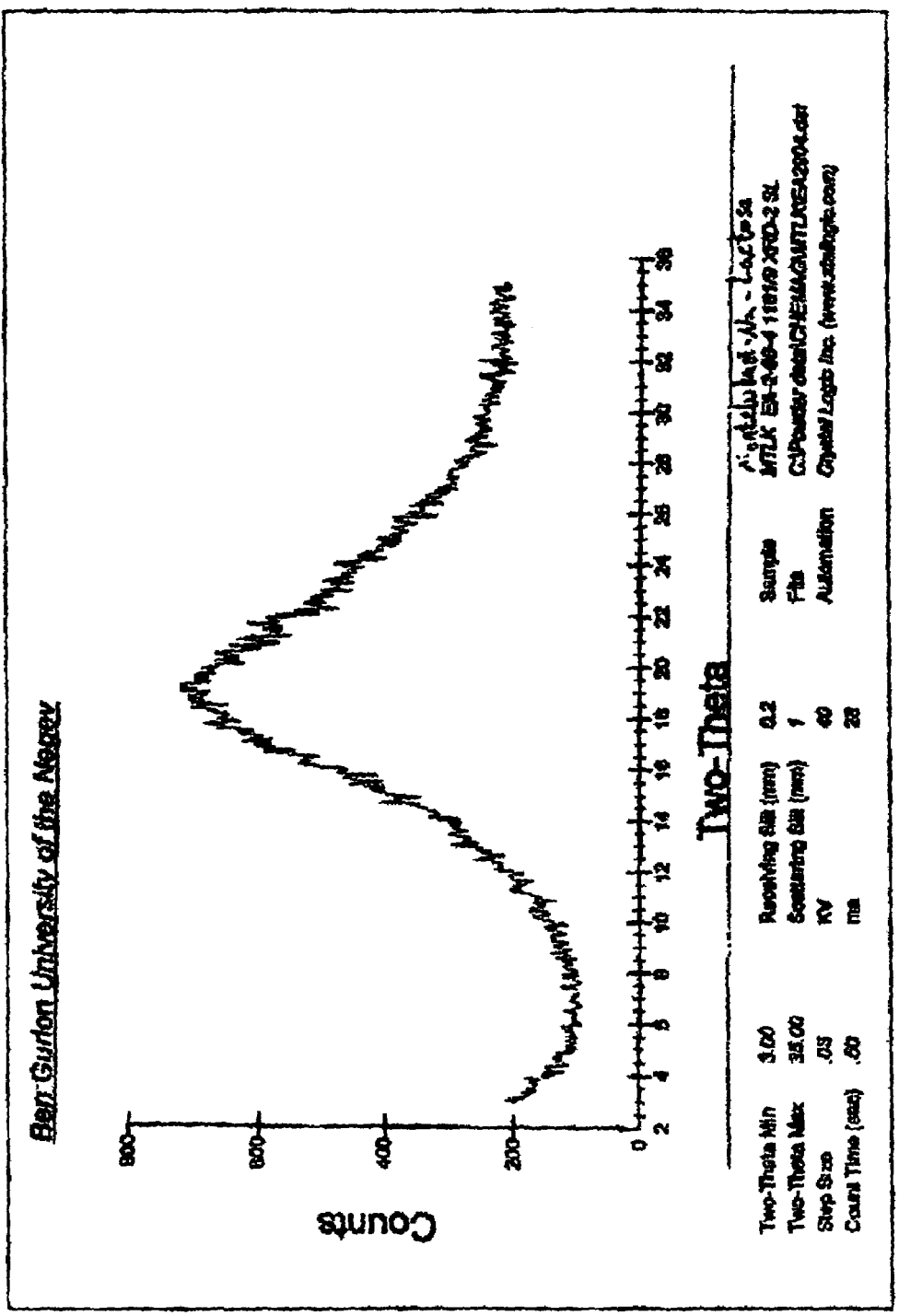
FIG. 4 presents an X-ray powder diffractogram of an exemplary co-precipitate of amorphous montelukast sodium and lactose according to the present invention prepared by freeze-drying and pressing at 10,000 Kg/cm$^3$ for 1 minute.

The X-ray analysis of the pressed residue gave a featureless diffractogram, as shown in FIG. 4, indicating that the residue remained amorphous.

The pressed residue was kept in open air having 30% humidity for 1 hour, so as to evaluate the change in the water content thereof and hence its hygroscopicity. The water content of the residue changed from 3.75% to 4.11%, showing a low degree of hygroscopicity.

Example 4

Amorphous Mixture of Montelukast Sodium and Lactose

Montelukast sodium (4.0 grams) and lactose monohydrate (12 grams) were dissolved in water (500 ml) and filtered. The solution was then lyophilized, producing a residue, which includes a co-precipitate of montelukast sodium and lactose, with a bulk density of 0.21 gram/cm$^3$.

The X-ray analysis of the residue gave a featureless diffractogram showing the residue was amorphous.

The residue was then pressed at 10,000 Kg/cm3 for 1 minute.

The X-ray analysis of the pressed residue gave featureless diffractogram, as shown in FIG. 6, indicating that the residue remained amorphous.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, the present invention is intended to embrace all such alternatives, modifications and variations that fall within the spirit and broad scope of the appended claims.

All publications, patents ad patent applications mentioned in this specification are herein incorporated in their entirety by reference into the specification, to the some extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A stable, non-hygroscopic, amorphous, free-flowing powder form of montelukast sodium.

2. The amorphous montelukast sodium of claim 1, wherein upon exposure to an atmosphere of about 30% humidity for a period of about one hour, the weight gain thereof is less than 2 weight percent of its total weight.

3. The amorphous montelukast sodium of claim 2, wherein said weight gain is less than 0.5 weight percent of its total weight.

4. The amorphous montelukast sodium of claim 1, which retains an amorphous character subsequent to storage at a temperature of at least 25° C. for a time period of at least 2 months.

5. The amorphous montelukast sodium of claim 4, which retains an amorphous character subsequent to storage at a temperature of about 40° C. for a time period of about 3 months.

6. The amorphous montelukast sodium of claim 1, having a bulk density greater than 0.10 g/cm$^3$.

7. The amorphous montelukast sodium of claim 1, having a bulk density greater than 0.20 g/cm$^3$.

8. The amorphous montelukast sodium of claim 1, having a bulk density that ranges between about 0.10 g/cm$^3$ and about 0.40 g/cm$^3$.

9. The amorphous montelukast sodium of claim 1, which retains an amorphous character subsequent to application of a pressure greater than 5000 Kg/cm$^3$ for a period of about one minute.

10. The amorphous montelukast sodium of claim 9, which retains an amorphous character subsequent to application of pressure of about 10000 Kg/cm$^3$ for a period of about one minute.

11. The amorphous montelukast sodium of claim 1, having a powder X-ray diffraction pattern substantially as depicted in FIG. 2.

12. A process of preparing the amorphous montelukast sodium of claim 1, the process comprising:
    dissolving montelukast sodium in a solvent, to thereby provide a solution of montelukast sodium in said solvent; and
    removing said solvent from said solution by spray drying, thereby obtaining the amorphous montelukast sodium.

13. The process of claim 12, wherein said solvent is selected from the group consisting of water, a water miscible organic solvent and a combination thereof.

14. The process of claim 13, wherein said water miscible organic solvent is selected from the group consisting of acetone, a $C_1$-$C_3$ alcohol, and any combination thereof.

15. The process of claim 13, wherein said water-miscible solvent is ethanol.

16. The process of claim 12, wherein said solvent is water.

17. The process of claim 12, wherein said solvent is ethanol.

18. The process of claim 12, wherein said solvent is a mixture of water and ethanol.

19. A pharmaceutical composition comprising the amorphous montelukast sodium of claim 1 and a pharmaceutically acceptable carrier wherein the amorphous character is maintained.

20. The pharmaceutical composition of claim 19, formulation in a solid dosage form.

21. The pharmaceutical composition of claim 20, wherein said solid dosage form is selected from the group consisting of a tablet, a capsule, a peel, a dragee, a powder and granules.

22. The pharmaceutical composition of claim 19, packaged in a packaging material and identified in print, in or on said packaging material, for treating a condition selected from the groups consisting of allergic rhinitis and asthma.

23. A method of treating a medical condition in which administration of montelukast sodium is beneficial selected from the group consisting of allergic rhinitis and asthma, the method comprising administering to a subject in need thereof a therapeutically effective amount of the pharmaceutical composition of claim 19.

24. The method of claim 23, wherein said administering is effected orally.

25. The method of claim 24, wherein said pharmaceutical composition is formulated in a solid dosage form.

26. An amorphous mixture of montelukast sodium and at least one pharmaceutically acceptable excipient wherein the amorphous character is maintained.

27. The mixture of claim 26, wherein said at least one pharmaceutically acceptable excipient comprises lactose.

28. The mixture of claim 27, wherein the ratio between the amorphous montelukast and lactose ranges between about 1:0.1 and about 1:10.

29. The mixture of claim 28, wherein said ratio ranges between about 1:0.5 and 1:2.

30. The mixture of claim 28, wherein said ratio is about 1:1.

31. The mixture of claim 26, wherein upon exposure to an atmosphere of about 30% humidity for a period of one hour, the weight gain thereof is less than 2 weight percent of its total weight.

32. The mixture of claim 31, wherein said weight gain is less than 0.5 weight percent of its total weight.

33. The mixture of claim 26, which retains an amorphous character subsequent to storage at a temperature of at least 25° C. for a time period of at least 2 months.

34. The mixture of claim 33, which an amorphous character subsequent to storage at a temperature of about 40° C. for a tine period of about 3 months.

35. The mixture of claim 26, having a bulk density greater than 0.10 gram/cm$^3$.

36. The mixture of claim 26, having a bulk density greater than t 0.20 gram/cm$^3$.

37. The mixture of claim 26, having a bulk density that ranges between about 0.10 gram/cm$^3$ and about 0.35 gram/cm$^3$.

38. The mixture of claim 26, which retains an amorphous character subsequent to application of pressure of greater than 5,000 kg/cm$^3$ for a period of about one minute.

39. The mixture of claim 38, which retains an amorphous character subsequent to application of pressure of about 10,000 Kg/cm$^3$ for a period of about one minute.

Figure 5:
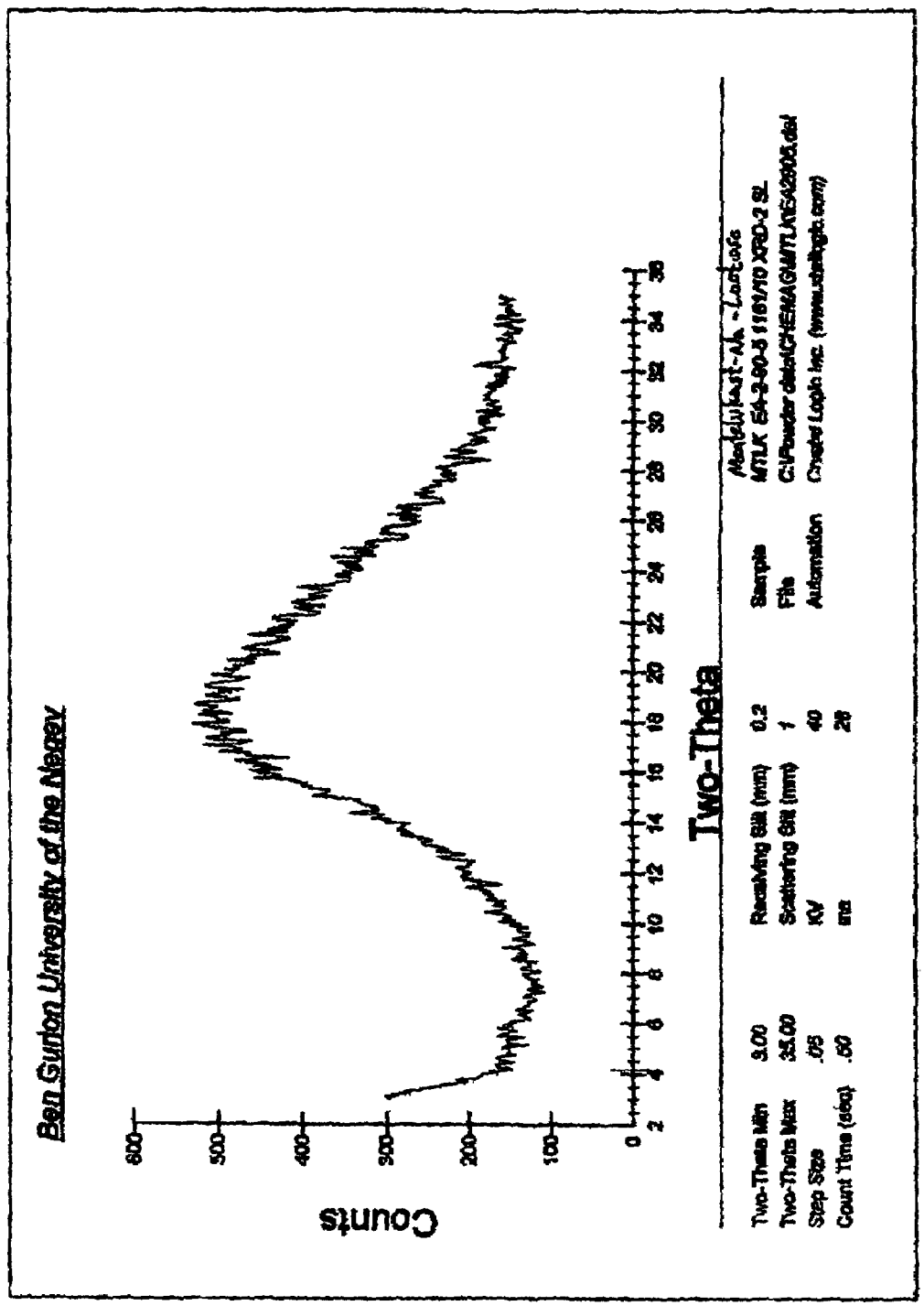
FIG. 5 present an X-ray powder diffractogram of an exemplary co-precipitate of amorphous montelukast sodium and lactose according to the present invention, prepared by freeze-drying and pressing at 10,000 Kg/cm$^3$ for 1 minute.

40. The mixture of claim 26, having a powder X-ray diffraction pattern substantially as depicted in FIG. 3, FIG. 4 or FIG. 5.

41. A process of preparing the mixture of claim 26, the process comprising:
dissolving montelukast sodium and at least one pharmaceutically acceptable excipient in a solvent, to thereby provide a solution of montelukast sodium in said solvent; removing said solvent from said solution, thereby obtaining the amorphous mixture of montelukast sodium and said at least one excipient.

42. The process of claim 41, wherein said at least one pharmaceutically acceptable excipient is lactose.

43. The process of claim 42, wherein said at least one pharmaceutically acceptable excipient is lactose monohydrate.

44. The process of claim 42, wherein a weight ratio between the amorphous montelukast and lactose ranges between about 1:0.1 and about 1:10.

45. The process of claim 42, wherein said weight ratio ranges between about 1:0.5 and 1:2.

46. The process of claim 42, wherein said ratio is about 1:1.

47. The process of claim 41, wherein said removing said solvent is effected by freeze drying said solution.

48. The process of claim 41, wherein said removing of said solvent is effected by spray drying said solution.

49. The process claim 41, wherein said solvent is selected from the group consisting of water, a water miscible organic solvent and a combination thereof.

50. The process of claim 49, wherein said water miscible organic solvent is selected from the group consisting of acetone, a C1-C3 alcohol, and any combination thereof.

51. The process of claim 49, wherein said water-miscible solvent is ethanol.

52. The process of claim 41, wherein said solvent is water.

53. The process of claim 41, wherein said solvent is ethanol.

54. The process of claim 41, wherein said solvent is a mixture of water and ethanol.

55. A pharmaceutical composition comprising the mixture of claim 26 and a pharmaceutically acceptable carrier wherein the amorphous character is maintained.

56. The pharmaceutical composition of claim 55, formulated in a solid dosage form.

57. The pharmaceutical composition of claim 56, wherein said solid dosage form is selected from the group consisting of a tablet, a capsule, a peel, a dragee, a powder and granules.

58. The pharmaceutical composition of claim 55, packaged in a packaging material and identified in print, in or on said packaging material, for treating a condition selected from the groups consisting of allergic rhinitis and asthma.

59. A method of treating a medical condition in which administration of montelukast sodium is beneficial selected from the group consisting of allergic rhinitis and asthma, the method comprising administering to a subject in need thereof a therapeutically effective amount of the pharmaceutical composition of claim 55.

60. The method of claim 59, wherein said administering is effected orally.

61. The method of claim 60, wherein said pharmaceutical composition is formulated in a solid dosage form.

* * * * *